United States Patent
Buysman et al.

(10) Patent No.: US 10,272,235 B2
(45) Date of Patent: Apr. 30, 2019

(54) DRUG RELEASING PELVIC TREATMENT SYSTEM AND METHOD

(71) Applicants: John Jason Buysman, Minnetonka, MN (US); Brian P. Watschke, Minneapolis, MN (US)

(72) Inventors: John Jason Buysman, Minnetonka, MN (US); Brian P. Watschke, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 573 days.

(21) Appl. No.: 14/981,128

(22) Filed: Dec. 28, 2015

(65) Prior Publication Data

US 2016/0144161 A1 May 26, 2016

Related U.S. Application Data

(63) Continuation of application No. 14/000,270, filed as application No. PCT/US2012/026362 on Feb. 23, 2012, now Pat. No. 9,233,238.

(Continued)

(51) Int. Cl.
*A61M 37/00* (2006.01)
*A61M 31/00* (2006.01)
(Continued)

(52) U.S. Cl.
CPC .......... *A61M 37/0069* (2013.01); *A61M 5/20* (2013.01); *A61M 31/00* (2013.01); *A61M 37/0015* (2013.01); *A61M 31/002* (2013.01); *A61M 2025/105* (2013.01); *A61M 2025/1086* (2013.01); *A61M 2037/0023* (2013.01); *A61M 2205/04* (2013.01)

(58) Field of Classification Search
CPC .......... A61M 37/0069; A61M 37/0015; A61M 2037/0046
See application file for complete search history.

(56) References Cited

U.S. PATENT DOCUMENTS

| 4,079,038 A | 3/1978 | Choi et al. |
| 4,138,344 A | 2/1979 | Choi et al. |

(Continued)

FOREIGN PATENT DOCUMENTS

| DE | 202006016866 U1 | 3/2007 |
| EP | 0 624 347 A1 | 11/1994 |

(Continued)

OTHER PUBLICATIONS

Rehabilitation Article "A Preliminary Clinical Study Using RF BION® Microstimulators Facilitate Upper Limb Function in Hemiplegia" ACNR, vol. 4, No. 2, pp. 26-28, May/Jun. 2004.

(Continued)

*Primary Examiner* — Andrew M Gilbert
(74) *Attorney, Agent, or Firm* — Brake Hughes Bellermann LLP (57) ABSTRACT

Various embodiments of a pelvic treatment system and method are provided. The present invention can include one or more drug eluting darts or barbs that are lodged into the wall and will elute the drug over a desired time period (weeks, months for example) to treat OAB, BPH, tissue weaknesses, or other disorders or diseases.

18 Claims, 7 Drawing Sheets

Related U.S. Application Data (60) Provisional application No. 61/445,807, filed on Feb. 23, 2011.

(51) Int. Cl.
  *A61M 5/20* (2006.01)
  *A61M 25/10* (2013.01)

(56) References Cited

U.S. PATENT DOCUMENTS

| | | | |
|---|---|---|---|
| 4,304,767 A | 12/1981 | Heller et al. | |
| 4,637,396 A | 1/1987 | Cook | |
| 4,651,721 A | 3/1987 | Mikulich et al. | |
| 4,900,304 A * | 2/1990 | Fujioka | A61M 37/0069 604/242 |
| 5,281,197 A * | 1/1994 | Arias | A61M 37/0069 604/209 |
| 5,542,920 A * | 8/1996 | Cherif Cheikh | A61M 37/0069 604/309 |
| 6,197,013 B1 | 3/2001 | Reed et al. | |
| 6,689,056 B1 * | 2/2004 | Kilcoyne | A61B 5/0031 128/898 |
| 6,962,574 B1 * | 11/2005 | Noblitt | A61B 17/3468 424/426 |
| 7,727,954 B2 * | 6/2010 | McKay | A61K 9/0024 424/130.1 |
| 7,837,670 B2 * | 11/2010 | Barath | A61M 25/0017 604/103.01 |
| 8,109,904 B1 | 2/2012 | Papp | |
| 8,160,710 B2 * | 4/2012 | Buysman | A61N 1/0558 607/41 |
| 8,353,863 B2 * | 1/2013 | Imran | A61M 37/0069 604/117 |
| 8,535,260 B2 * | 9/2013 | Kassab | A61K 9/0024 424/426 |
| 9,233,238 B2 * | 1/2016 | Buysman | A61M 37/0069 |
| 9,555,228 B2 * | 1/2017 | Kassab | A61K 9/0024 |
| 2004/0067235 A1 | 4/2004 | Doshi | |
| 2004/0124105 A1 * | 7/2004 | Seiler | A61M 37/0069 206/363 |
| 2004/0175408 A1 | 9/2004 | Chun et al. | |
| 2006/0224237 A1 | 10/2006 | Furst et al. | |
| 2007/0123973 A1 | 5/2007 | Roth et al. | |
| 2007/0135803 A1 | 6/2007 | Belson | |
| 2007/0191811 A1 * | 8/2007 | Berglund | A61M 25/104 604/509 |
| 2008/0228193 A1 * | 9/2008 | Matityahu | A61K 9/0024 606/99 |
| 2010/0069837 A1 | 3/2010 | Rassat et al. | |
| 2010/0094256 A1 * | 4/2010 | Kassab | A61K 9/0024 604/514 |
| 2010/0105979 A1 * | 4/2010 | Hamel | A61B 17/0401 600/30 |
| 2010/0204678 A1 * | 8/2010 | Imran | A61M 37/00 604/511 |
| 2011/0034860 A1 | 2/2011 | Melsheimer | |
| 2011/0160699 A1 | 6/2011 | Imran | |
| 2012/0041412 A1 * | 2/2012 | Roth | A61M 25/10 604/500 |
| 2013/0331783 A1 * | 12/2013 | Herman | A61M 25/10 604/103.08 |
| 2015/0151077 A1 * | 6/2015 | Harrington | A61M 37/0069 604/506 |

FOREIGN PATENT DOCUMENTS

| | | |
|---|---|---|
| EP | 0 655 225 A1 | 5/1995 |
| GB | 2 094 636 A | 9/1982 |
| GB | 2 151 484 A | 7/1985 |
| GB | 2 226 497 A | 7/1990 |
| GB | 2 244 922 A | 12/1991 |
| GB | 2 283 678 A | 5/1995 |
| JP | 11-333005 | 12/1999 |
| JP | 2005312964 | 11/2005 |
| SU | 1 336 892 | 11/1973 |
| WO | WO 03/096929 | 11/2003 |
| WO | WO 2004/012626 | 2/2004 |
| WO | WO 2007/097994 | 8/2007 |
| WO | WO 2007/149555 | 12/2007 |
| WO | 2009033026 | 3/2009 |
| WO | 2012083155 | 6/2012 |

OTHER PUBLICATIONS

Caldwell et al, "Stress Incontinence in Females: Report on 31 Cases Treated by Electrical Implant" J. Obstet, Gynaec. Brit. Cwlth., vol. 75, pp. 777-780, Jul. 1968.
Cavouto, "BION Developers Pus-h New Versions and Applications" BION Developments, Neurotech Business Report, pp. 1-2, Jul. 2005, http://www.neurotechreports.com-/pages/BION.html.
ClinicalTrials.gov, I-STOP TOMS—Trans Obturator Male Sling, May 2008, http://clinicaltrials.gov/ct2/show/NCT00442078.
Igel, et al., "Comparison of Techniques for Vesicourethral Anastomosis: Simple Direct Versus Modified Vest Traction Sutures" Urology, Vo. XXXI, No. 6, pp. 474-477, Jun. 1988.
Iglesia, et al. "The Use of Mesh in Gynecologic Surgery" Int Urogynecol J. 8: pp. 105-115, 1997.
JS Krauth, et al. "La bandelette trans obturatrice dans le traitement de l'incontinence urinaire feminine" Tire-a-part ENDOMAG No. 47, pp. 13-15, Jun. 2004.
JS Krauth, et al., "The Trans-Obturator Tape for the Treatment of Female Stress Urinary Incontinence—Multicentre Study of 140 cases—The Learning Curve—Morbidity-".
O'Donnell, M.D., Urinary Incontinence Mosby-Year Book, Inc., International Standard Book No. 0-8151-6517-X, pp. 197-202, 1997.
Pavelic et al., "Liposomal gel with chloramphenicol: characterization and in vitro release," Acta. Pharm. 54 (2004) 319-330.
Swain (Cover Story) Breakthrough products could put lesser-known firms on the map (MDDI archive, Apr. 2004), originally published MDDI Apr. 2004, http://www.devicellnk.com/mddi/archive/04/04/006.html, Jul. 2005.
Medical News Today New Article "Uroplasty Inc. and CL Medical Announce FDA Clearance of I-Stop™ TOMS Sling for Treatment of Male Stress Urinary Incontinence" pp. 1-2, Nov. 2006, Article URL: http://www.medicalnewstoday.com/articles/57663.php.
Vermani et al., "The scope and potential of vaginal drug delivery," PSIT, vol. 3, No. 10, pp. 359-365 (Oct. 2000).
Organ, S.J., "Phase separation in blends of poly(hydroxybutrate) with poly(hydroxybutrate-co-hydroxyvalerate): variation with blend components" Polymer, vol. 35, No. 1, pp. 86-92, 1994.
Gassner, et al., "Physical properties of PHB-PCL" Polymer, vol. 35, No. 10, pp. 2233-2236, 1994.
Wolf, F.K., et al., "Poly(glycolide) multi-arm star polymers: Improved solubility via limited arm length" *Beilstein J. Org. Chem.* 6, No. 67, pp. 1-9, 2010.

* cited by examiner

DRUG RELEASING PELVIC TREATMENT SYSTEM AND METHOD

PRIORITY CLAIM

This application is a continuation of Ser. No. 14/000,270, filed Aug. 19, 2013, now U.S. Pat. No. 9,233,238, which claims the benefit from International No. PCT/US2012/026362, which was granted an International Filing date of Feb. 23, 2012, which in turns claims priority under 35 U.S.C. § 119(e) from United States Provisional Patent Application having U.S. Ser. No. 61/445,807, filed Feb. 23, 2011, entitled "DRUG ELUTING PELVIC TREATMENT SYSTEM AND METHOD", the entireties of these patent applications being incorporated herein by reference.

FIELD OF THE INVENTION

The present invention relates generally to surgical methods and apparatus and, more specifically, to implantable devices adapted to provide therapeutic treatment to pelvic tissue or organs.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia hi which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUE) occurs when the patient is physically stressed.

Treatments using Botox are available for Overactive Bladder (OAB). For this treatment standard needles and syringes are used to inject Botox into the bladder wall through a catheter. Several injections need to be made over the desired treatment area like nodes on a grid pattern. Obviously, the use of injections, single or multiple, can be difficult, time consuming and potentially increase the occurrence of human error.

There is a desire to obtain a minimally invasive yet highly effective implantable treatment device that can be used to over active bladder (OAB) syndrome and other conditions.

SUMMARY OF THE INVENTION

The present invention describes therapeutic agent delivery systems and methods for treating pelvic conditions such as active bladder (OAB) syndrome, bladder infection, bladder cancer, incontinence, prostrate disease, uterine fibroids, abnormal uterine bleeding, endometriosis, and other conditions caused by tissue weaknesses, disease, or other abnormalities. As a general matter, the delivery system and methods, unlike conventional injection methods and devices, uses an alternative way to deliver therapeutic agent into pelvic tissue, such as into the bladder wall, vaginal wall, or the endometrial tissue of the uterus. The system and methods can use one or more tissue penetrating members, such as darts or barbs, that are lodged into the target pelvic tissue and that release a therapeutic agent over a desired time period, such as over the course of weeks or months.

In one embodiment, the invention provides a system for delivering a therapeutic agent to a pelvic tissue that comprises a delivery device configured for insertion through a pelvic passageway in a patient. The device has a distal end comprising an expandable elastic portion having a tissue-contacting surface configured to come in contact with pelvic tissue. Tissue penetrating members project from the tissue-contacting surface of the expandable elastic portion, the tissue penetrating members configured for detachment from the expandable elastic portion after the members have penetrated the pelvic tissue. Tissue penetrating members include a therapeutic agent that is released following implantation of the members in the tissue to treat the condition.

The invention also provide a method for delivering a therapeutic agent to a pelvic tissue in which the system comprising the expandable elastic portion is delivered to a target pelvic tissue in a patient, and then expanded so the tissue-contacting surface comes in contact with the target pelvic tissue and the tissue penetrating members enter the pelvic tissue. The tissue penetrating members are then allowed to become detached from the expandable elastic portion and reside in the target tissue. Therapeutic agent is then released from the tissue penetrating members to treat the condition.

In further embodiment, the invention provides another system for delivering a therapeutic agent to a pelvic tissue. The system includes a delivery device configured for insertion through the pelvic area passageway in a patient and delivery of tissue penetrating members to a pelvic tissue. The device comprises a lumen, a distal end, and an ejection member for forcing the tissue penetrating members out of the distal end. A series of tissue penetrating members are loaded in the lumen in a proximal to distal arrangement, with the tissue penetrating members configured for deployment from the distal end of the device and penetration into pelvic tissue. The tissue penetrating members include a therapeutic agent.

The invention also provides a method for delivering a therapeutic agent to a pelvic tissue in which the distal end of the device is delivered to a target pelvic tissue, and a tissue penetrating member ejected from the distal end into pelvic tissue. The distal end of the delivery device is moved to a different tissue location, and the step of ejection is repeated.

Therapeutic agent is allowed to be released from the tissue penetrating members in the tissue.

DETAILED DESCRIPTION OF PREFERRED EMBODIMENTS

Referring generally to FIGS. 1-9, various embodiments of system and devices for delivering a therapeutic agent to a pelvic tissue are shown, for treatment of a pelvic tissue disorder. The pelvic implants can release therapeutic agent to provide therapeutic benefits for the surrounding tissue. The delivery system and methods use one or more tissue penetrating members that are released from a portion of the delivery device, and become implanted into target pelvic tissue. Over time, a therapeutic agent is released and produces a desired effect in the tissue area the tissue penetrating members are implanted in.

Figure 1:
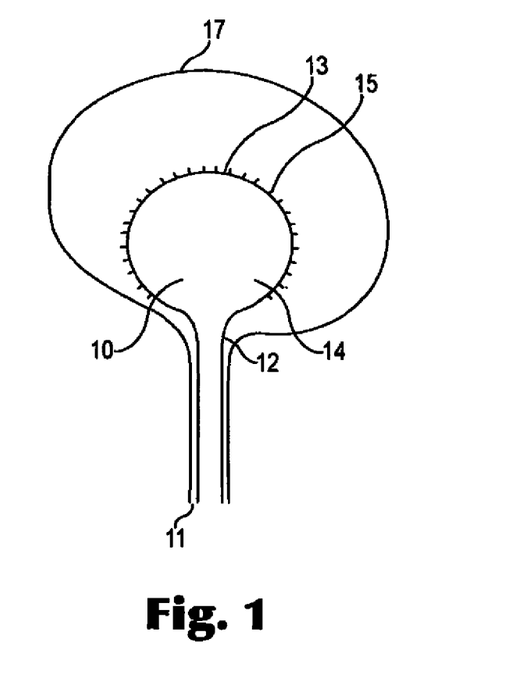
FIG. 1 is an illustration of a delivery device having distal end balloon with drug-containing tissue penetrating members on its surface, partially inflated in a patient bladder.

FIG. 1 shows a delivery system 10 that includes a catheter tube 11 shown within the urethra 18 of a patient. The distal end 12 of the catheter tube 11 is attached to a catheter balloon 14, which is shown as partially inflated within the bladder 17 of a patient that is being treated. The catheter balloon 14 has a tissue-contacting surface 13 on which are attached tissue penetrating members 15. All or a portion of the tissue-contacting surface 13 can be covered with tissue penetrating members 15. The location of the tissue penetrating members 15 can be determined by the areas in the target tissue in need of treatment. Also, the dose of the therapeutic agent can be controlled by the density of tissue penetrating members 15 on the tissue-contacting surface 13.

The catheter tube 11 can be made from a flexible material, sufficient to be manipulated and bent during insertion into the urethra. Exemplary flexible materials which can be made into catheter tubing include rubber, polyvinylchloride (PVC), polyurethane (PU), silicone, and polyester, which can provide adequate rigidity and flexibility for the insertion process. The surface of the catheter can also have a lubricant applied to the surface, such as silicone oil, or can have a thin lubricious coating, such as a hydrogel coating on the device surface, to facilitate insertion by reducing frictional forces on the surface.

The catheter tube can have dimensions suitable for insertion and operation of the inflatable balloon in the bladder. Common sizes of urethral catheters range from 10 French to 28 French (F) (1 F=0.33 mm), with sizes in the range of 12 F-16 F being common for use in adult humans, and having an inner diameter (lumen) in the range of about 1-3 mm.

The catheter can be adapted for either male or female use. Some urethral catheters are referred to as "Foley catheters," and catheters of these types can be modified to provide the desired features in accordance with aspects of the invention. Normally, a urethral catheter tube is navigated through the urethra so urine can be drained from the bladder from the distal end of the catheter tube, which is located within the bladder. The catheter tube of delivery devices of the current invention can include a drainage lumen for urine, in addition to a separate lumen for providing an air or a liquid for inflation of the balloon (e.g., an inflation lumen). The balloon 14 can be attached to the distal end 12 of the catheter tube 11 and in fluid or gaseous communication with the inflation lumen. The proximal end (not shown) of catheter tube 11 has features for controlling movement of the catheter and balloon during insertion, and controlling inflation of the balloon.

The balloon 14 can be formed from a suitable elastomeric material such as natural rubber, synthetic rubber, including styrene-butadiene copolymers, polyisoprene, isobutylene-isoprene copolymers (butyl rubber), including halogenated butyl rubber, butadiene-styrene-acrylonitrile copolymers, silicone and fluorosilicone elastomers, polyvinylchloride, polyester, or polyurethane, and polyamides. Combinations of more than one elastomeric material can be used to make the balloon. Multi-layered balloon constructions can also be used. Exemplary multi-layered balloon constructions are described in various references such as U.S. Pat. No. 4,637,396 which describes a three layer wall, and in U.S. Pat. No. 4,651,721. Many manufacturing processes for catheter balloon construction involve molding of thermoplastic material. For example thermoplastic material can be expanded in association with a mold to provide a balloon that in its inflated configuration has the shape of the inside of a bladder.

The catheter balloon can be constructed to have a cross-sectional thickness of the elastic material that is appropriate for the therapeutic agent delivery method and apparatus. Exemplary thicknesses of the elastic material range from about 5 µm to about 100 µm, and more specifically are in the range of about 5 µm to about 25 µm. The thickness refers to the elastic balloon material and does not take into consideration the length of the therapeutic agent-containing members that are attached to the tissue-contacting surface of the balloon. The cross-sectional thickness of the elastic material can vary based on factors such as the balloon's pressure ranking, expansion attributes, and pliability.

Figure 2A:
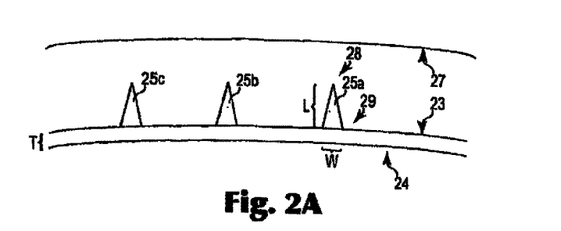
FIGS. 2a-2c are illustrations of the transfer of drug-containing tissue penetrating members from a balloon surface to a target tissue.
Figure 2B:
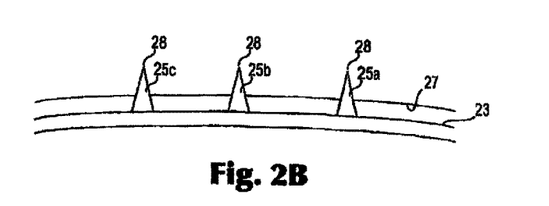
Figure 2C:
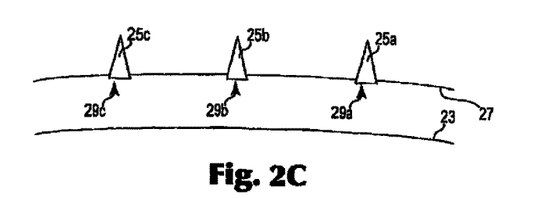

Portions of the catheter balloon with attached tissue penetrating members are discussed in more detail with reference to a cross-section of the balloon in FIG. 2. Referring to FIG. 2a, the elastomeric material of the balloon has a thickness (T), a tissue-contacting surface 23, an inner surface 24. Each tissue penetrating member (25a-25c) has a length (L) from its distal end 28 to its proximal end 29, and an average width (W) as calculated over the entire length of the member. FIG. 2a shows the proximal end 29 of the member is attached to the tissue-contacting surface 23 of the balloon, but in other arrangements the proximal end 29 can be located within the elastomeric material of the balloon, at the inner surface 24 of the balloon, or with the inner space of the balloon.

In various embodiments of the invention, and with reference to FIGS. 2-7, the tissue penetrating members that include a therapeutic agent are initially attached to the material of the balloon during the delivery process, such as reflected in FIG. 2a. During the delivery process, as illustrated in FIG. 2b, the tissue penetrating members become lodged in the tissue by pushing the distal end 28 of the member into the tissue. The tissue surface 27 can become flush with the tissue-contacting surface 23 of the balloon during the implantation process. The tissue penetrating members can then enter the tissue so that the entire length L, or a portion of the length L, is within the tissue. After the tissue penetrating members have penetrated to a sufficient depth in the tissue, the balloon is withdrawn from the tissue surface 27, as shown in FIG. 2c. The proximal ends (29a-29c) of the tissue penetrating members (25a-25c) become detached from the tissue-contacting surface 23. The balloon is then removed from the treatment area and the tissue penetrating members release therapeutic agent into the tissue over a desired time period.

The invention also contemplates various shapes, configurations, and surface features of tissue penetrating members as shown in FIGS. 2-7. For example, in various configurations, the tissue penetrating members can have a shape that resembles a dart, a barb, a spear, a spike, a lance, or an arrow point. As such, the member can include a conical, pyramidal, or rod shape. Generally, a distal end of a tissue penetrating member (e.g., distal end 28 of member 25a in FIG. 2a) can be sharpened to facilitate entry of the member into the tissue. The sharpening can be reflected by a beveled, a pointed, or tapered end. The member can have a diameter or cross sectional area at its distal end 28 that is less than the diameter or cross sectional area at its proximal end 29.

The member can also be described in terms of dimensional attributes such as height, width, cross sectional area, volume, etc. For example, in some embodiments, the member has a height in the range of about 50 µm to about 2000 µm, about 100 µm to about 1500 µm, about 200 µm to about 1000 µm, or about 250 µm to about 750 µm.

An average diameter or cross sectional area for the member can also be determined. If the member has a pointed shape, the diameter or cross sectional area can change from the proximal to distal end, and the average diameter or cross sectional area can be determined knowing the shape and dimensions of the member. For example, in some embodiments, the member has an average diameter in the range of about 15 µm to about 1000 µm, about 25 µm to about 750 µm, about 50 µm to about 500 µm, or about 100 µm to about 250 µm. In some embodiments, the member has an average cross-sectional area in the range of about 175 µm² to about 0.785 mm², 490 µm² to about 0.440 mm², about 1950 µm² to about 0.195 mm², or about 7850 µm² to about 50,000 µm².

The volume of the member can also be described. In some embodiments, the member has a volume in the range of about 3000 µm³ to about 0.55 mm³, 0.01 mm³ to about 0.45 mm³, or 0.05 mm³ to about 0.45 mm³.

Figure 3A:
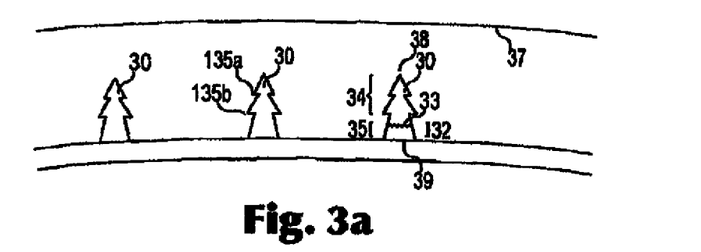
FIGS. 3a-3c are illustrations of the transfer of drug-containing tissue penetrating members from a balloon surface to a target tissue.

The member can also have features that facilitate its implantation in the target tissue. Once the member penetrates into the tissue, such features can prevent the member from becoming dislodged, or moving in the opposite direction from which the member was introduced. For example, as shown in FIG. 3a, the member can include one or more projections (135a and 135b; e.g., tines or barbs) on the lateral or elongate surface of the tissue penetrating member which are directed outward and towards the proximal end of the member. The projections prevent backwards movement of the member once in the tissue.

The invention contemplates various arrangements and constructions for associating the tissue penetrating members with the balloon material, and releasing the members after they have penetrated into tissue. For example, one approach uses a tissue penetrating member that has a fracturable portion near the proximal end of the penetrating member. The fracturable portion can have a material or structural weakness that causes the tissue penetrating member to break near its proximal end so it can be released from the elastic substrate.

Figure 3B:
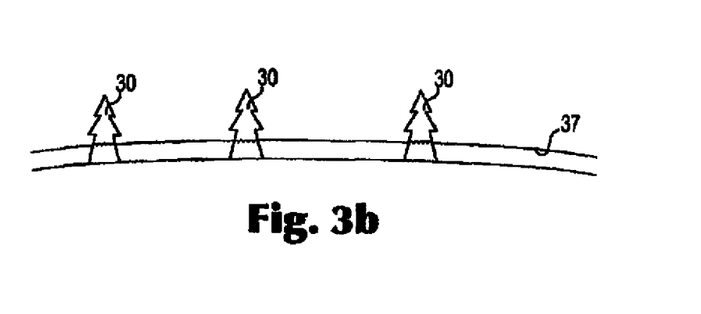
Figure 3C:
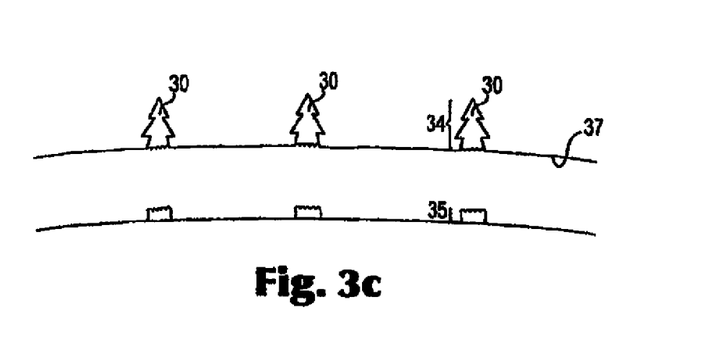

For example, with reference to FIG. 3a, the tissue penetrating member 30 has a fracturable portion 32 that is near the proximal end of the member. The fracturable portion can be formed by treating the tissue penetrating member in this area such as to weaken the material. Alternatively, the tissue penetrating member can be constructed from two different materials that are weakly bonded or adhered to each other. For example, the tissue penetrating member is constructed of a first material in portion 34 towards the distal end 38 of the member, and of a second material in portion 35 towards the proximal end 39 of the member. First and second materials are weakly bonded or adhered to each other in the member, and the member is breakable at the point where these two materials meet. As illustrated in FIG. 3b, the tissue penetrating members become lodged in the tissue, and the surface projections 135a and 135b hinder their movement out of the tissue. When the balloon is withdrawn from the tissue surface 37, as shown in FIG. 3c, the tissue penetrating members fracture at fracturable portion 32 and portion 34 remains lodged in the tissue, while portion 35 remains with the balloon surface. The balloon is then removed from the treatment area and the tissue penetrating members release therapeutic agent into the tissue over a desired time period.

Figure 4:
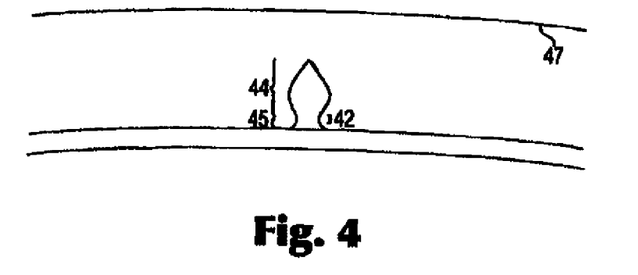
FIGS. 4-6 are illustrations of drug-containing tissue penetrating member on a balloon surface.

In another configuration, with reference to FIG. 4, the tissue penetrating member has a fracturable portion 42 having a cross sectional area that is less than a cross sectional area in portion 44 distal to the fracturable portion 42. Similar to the method as reflected in FIGS. 3b and 3c, after the tissue penetrating members are lodged in the tissue, and when the balloon is withdrawn from the tissue surface 47, the tissue penetrating members fracture at fracturable portion 42 and portion 44 remains lodged in the tissue, while portion 45 remains with the balloon surface. The balloon is then removed from the treatment area and the tissue penetrating members release therapeutic agent in to the tissue over a desired time period.

Figure 5:
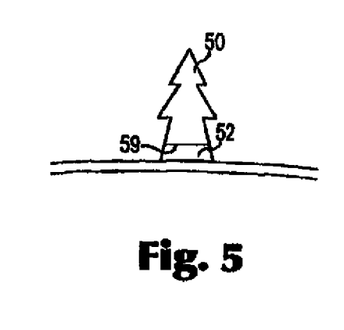
Figure 6:
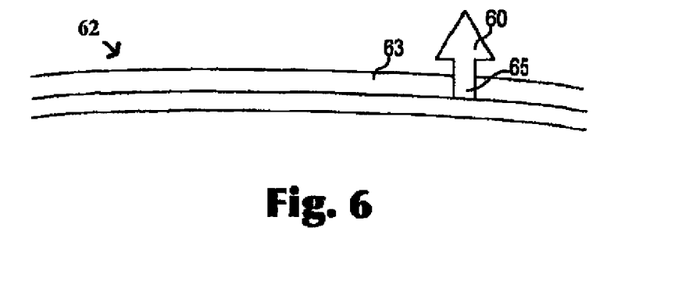
Figure 7A:
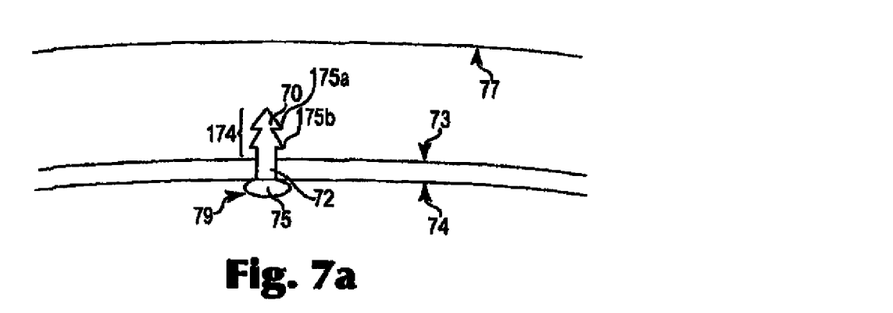
FIG. 7a-7c are illustrations of the transfer of drug-containing tissue penetrating members from a balloon surface to a target tissue.
Figure 7B:
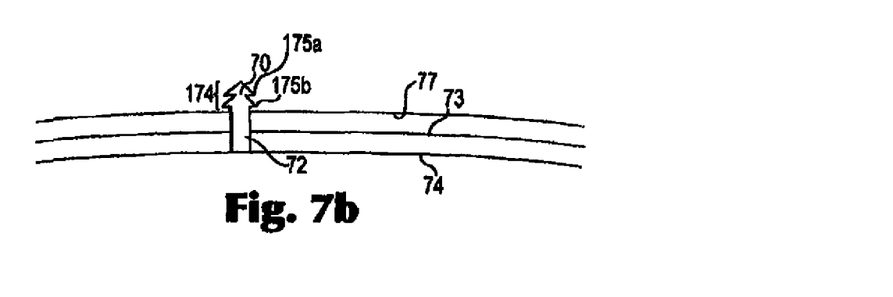
Figure 7C:
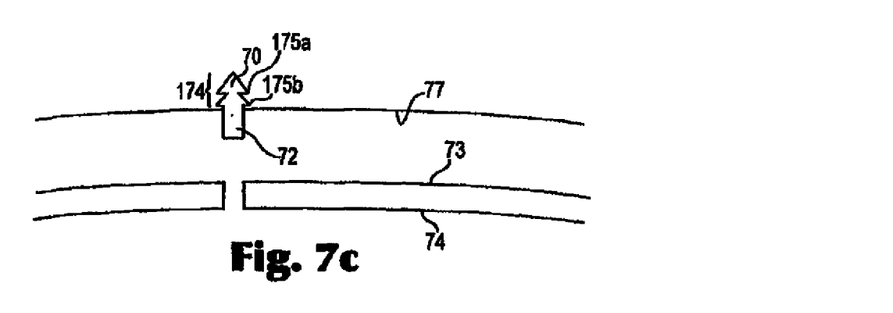

In other constructions, such as shown in FIGS. 5-7, the tissue penetrating member is attached to the elastic portion using an absorbable (degradable) material. Generally, the absorbable material is used to attach the tissue penetrating member during the delivery process, and then it undergoes degradation during the process to weaken or remove the absorbable material, which loosens the tissue penetrating member from the surface of the device to that it can be released into tissue.

For example, referring to FIG. 5, the proximal end 59 of the tissue penetrating member 50 is attached to the surface of the balloon using an absorbable material 52, such as an absorbable polymer, that acts as a temporary adhesive. During the delivery process, during which the tissue penetrating member 50 becomes lodged into target tissue, the absorbable material partially or completely erodes so that the member is detached from the elastic surface. The erosion can result in weakening of the absorbable material 52 so that it fractures, similar to the mechanisms discussed with reference to FIG. 4.

As another example, referring to FIG. 6, a proximal portion 65 of the tissue penetrating member 60 is partially embedded in a layer of absorbable material 63 formed on the surface of the balloon 62. During the delivery process, during which the tissue penetrating member 60 becomes lodged into target tissue, the layer of absorbable material 63 absorbable material partially or completely erodes so that the proximal portion of the tissue penetrating member 60 is loosened and detaches from the elastic surface.

As another example, referring to FIG. 7a, the tissue penetrating member 70 comprises a proximal portion 72 that traverses material of balloon. The tissue penetrating member 70 has a distal portion 174 that is on the tissue-contacting surface 73 of the balloon. The proximal end 79 of the tissue penetrating member 70 is on the inner surface of the balloon 74 and is associated with an absorbable material 75 which allows the tissue penetrating member 70 to be fastened to the balloon. As illustrated in FIG. 7b, the portion 174 of the tissue penetrating member becomes lodged in the tissue, and the surface projections 175a and 175b hinder movement of the member out of the tissue. Further, the inner surface of the balloon 74 can be treated to cause erosion of the absorbable material 75. For example, a liquid composition that is acidic can be delivered to the inner space in the balloon, and the low pH condition can enhance erosion of the polymeric material.

When the balloon is withdrawn from the tissue surface 77, as shown in FIG. 7c, proximal portion 72 of the tissue penetrating member is able to be withdrawn from the balloon and portion 174 remains lodged in the tissue. The balloon is then removed from the treatment area and the tissue penetrating members release therapeutic agent into the tissue over a desired time period.

The absorbable material used to fasten the tissue penetrating member 70 can be one that is has sufficient adhesion strength, but that dissolves or erodes quickly after the tissue penetrating member has been lodged in the tissue. For example a non-crosslinked polysaccharide, or a rapidly eroding polymer such as a polyorthoester or a poly(lactide-co-caprolactone) polymer can be used to fasten the tissue penetrating member to elastic material of the balloon.

The tissue penetrating member can be formed from one or a combination of biocompatible materials along with a therapeutic agent. Various types of absorbable polymeric materials can be used to modulate release of therapeutic agent from the tissue penetrating members. The terms "bioabsorbable," "degradable," and "biodegradable," can also be used to describe a material that is absorbable, such as an absorbable polymer. Many absorbable polymers include hydrolytically unstable chemical groups such as ester groups in the polymeric backbone. The hydrolytic cleavage of these chemical groups leads to degradation of the polymer. Absorbable polymers, such as those described in Table 1, can be used in any of the embodiments of the invention.

TABLE 1

Polyhydroxyalkanoates (e.g., poly-4-hydroxybutyrate (P4HB), poly(3-hydroxyvalerate, poly(hydroxybutyrate-co-hydroxyvalerate); polyesters (e.g., polylactic acid, poly(lactide-co-glycolide), polycaprolactone, poly(valerolactone), poly(glycolic acid), (poly(glycolide)), and poly(dioxanone); polyorthoesters; polyalkeneanhydrides (e.g., poly(sebacic acid); polyanhydrides, polyphosphazine.
Hyaluronic acid, alginate, dextran, starch, amylopectin, cellulose, xanthan, pullulan, chitosan, pectin, inulin, and heparin.

Polyhydroxyalkanoates include homopolymers such as poly-4-hydroxybutyrate (P4HB), poly(3-hydroxyvalerate), and hydroxyalkanoate copolymers such as poly(hydroxybutyrate-co-hydroxyvalerate) (Organ, S. J. (1994) Polymer, 35, 1:86-92) Blends of hydroxyalkanoate polymers with other absorbable polymers have also been prepared, such as poly(β-hydroxybutyrate) and poly(ε-caprolactone) blends (Gassner, F., and Owen, A. J. (1994) Polymer, 35, 10:2233-2236).

Poly(glycolic acid) (PGA) is a highly crystalline and has a melting point in the range of 225-230° C. While higher molecular weight forms are insoluble in common organic solvents such as acetone, dicholomethane, chloroform, and tetrahydrofuran, its lower molecular weight forms generally have better solubility in common organic solvents. Glycolide copolymers also can have better solubility in common organic solvents. For example, star block copolymers based on glycerol and glycolide show solubility in organic solvents such as DMF and DMSO (see, for example, Wolf, F. K., et al. (2010) *Beilstein J. Org. Chem.* 6, No. 67). Copolymers of lactic acid and glycolic acid (e.g., 50:50 mol percent) have solubility in chloroform (U.S. Pat. No. 3,867,190). Copolymerization of lactic acid and glycolic acid reduces the degree of crystallinity and results in an increased rate of hydration and hydrolysis. Copolymers of lactic acid and glycolic acid can be manipulated into a desired form by techniques such as extrusion, injection and compression molding as well as particulate leaching and solvent casting.

Lactic acid is a chiral molecule and L-lactide and D-lactide optically active forms can be polymerized to form poly-L-lactide (PLLA), poly-D-lactide (PDLA), and poly-D,L-lactide (PDLLA). PLLA has a crystallinity of about 37%, a glass transition temperature between 60-65° C., and a melting temperature between 173-178° C. PDLLA is amorphous and has a glass transition temperature of 55-60° C.

Another polyester, polydioxanone (PDS) is made by a ring-opening polymerization of the p-dioxanone monomer that forms a polymer of multiple repeating ether-ester units. PDS has a glass transition temperature in the range of −10 to 0° C. and a degree of crystallinity of about 55%. The presence of an ether oxygen within the polydioxanone backbone of the polymer chain can provide materials with enhanced flexibility.

Exemplary erodible polyorthoesters can be formed by reacting an orthoester (or orthocarbonate) with a diol (see, for example, U.S. Pat. Nos. 4,079,038, and 4,138,344), or by reacting a reacting a polyol with a polyfunctional ketene acetal (see, for example, U.S. Pat. No. 4,304,767).

In many cases, the degradation rate of a homopolymer (i.e., one formed from a particular monomer type is) slower than copolymer (formed from the particular monomer a different monomer). Various embodiments of the invention can use copolymers and homopolymers, which share a common monomer type, to form the tissue penetrating members.

The tissue penetration members can be fabrication by various process, such as by molding. For example, a composition including an absorbable polymer, a therapeutic agent, and a solvent can be disposed in a mold to cast a tissue penetration member with a desired shape. Solvent can be removed to harden the member. The tissue penetration member can then be removed from the mold and associated with the elastic substrate of the device. In some modes of fabrication, the tissue penetration member can be pulled out of the mold using the elastic substrate.

Exemplary therapeutically-active compounds include steroid hormones, antimuscarinic agents, antiproliferative agents, angiogenesis inhibitors, anti-inflammatory agents, anti-cancer drugs, anti-fibrotic agents, anti-microbial agents, immunosuppressive agents, antibiotics, etc.

Therapeutic agents having a steroid ring system are referred to as steroids, which can include naturally occurring compounds and synthetic analogues based on steroid ring structures. Steroids which can be used in the therapeutic agent-releasing implant include glucocorticoids, estrogens and androgens. Exemplary therapeutic agents, including those listed herein, can be associated with and released from various embodiments of therapeutic agent-releasing implants as described herein.

In some systems and methods, the therapeutic agent comprises a compound that affects nerve function. One class of compounds that affect nerve function are antimuscarinic compounds that affect the activity of the muscarinic acetylcholine receptor. Antimuscarinic agents include those such as oxybutynin, tolterodine, solifenacin, and hyoscyamine. Another class of therapeutic agents that affects nerve function is nerve toxins. An exemplary nerve toxin is such as Botulinum toxin. Antimuscarinic compounds and nerve toxins is such as Botulinum toxin can be releasable from the tissue penetrating members of the invention, and can be used to treat over active bladder syndrome.

In some systems and methods, the therapeutic agent comprises a chemotherapeutic compound. Chemotherapeutic agents include those such as N,N',N'-triethylenethiophosphoramide (ThioTEPA), adriamycin (doxorubicin, ADM), epirubicin (EPI), mitomycin C (MMC), valrubicin (AD32), pirarubicin (THP), gemcitabine, apaziquone (EOquin™), and Vicinium™ (anti-Ep-CAM humanized scFv-exotoxin A fusion protein). Chemotherapeutic agents can be releasable from the tissue penetrating members of the invention, and can be used to treat various tumors and cancers, including those of the bladder, prostrate, cervical, rectal, anal, and vaginal tissues.

In some systems and methods, the therapeutic agent comprises an antiproliferative agent or angiogenesis inhibitor such as taxol, rapamycin, tacrolimus, ABT-578, everolimus, paclitaxel, taxane, 13-cis retinoic acid, and 5-fluorouracil. Antiproliferative agents or angiogenesis inhibitors can be releasable from the tissue penetrating members of the invention, and can be used to treat abnormal pelvic tissue growth, including various cancers of the pelvis.

In some systems and methods, the therapeutic agent comprises a steroid such as dexamethasone, cortisone, hydrocortisone, prednisone, prednisolone, triamcinolone methylprednisolone, beclomethasone, betamethasone, chloroprednisone, corticosterone, desoxycorticosterone, estradiol, fluorocortisone, androsterone, aldosterone, methyl testosterone, norethandrolone, estriol, estrone, hydroxyprogesterone. Steroids can be releasable from the tissue penetrating members of the invention, and can be used to treat tissue disorders of the female reproductive tract, such as abnormal uterine bleeding, to promote wound healing and thickening of thin tissues.

In some systems and methods, the therapeutic agent comprises an antibiotic such as amoxicillin, ephalexin, cefadroxil, cefuroxime, loracarbef, cefixime, pivmecillinam, trimethoprim-sulfamethoxazole, trimethoprim, ofloxacin, ciprofloxacin, norfloxacin, levofloxacin, doxycycline, tetracycline, minocycline, gentamicin, tobramycin, amikacin, nitrofurantoin, or azithromycin. Antibiotics can be releasable from the tissue penetrating members of the invention, and can be used to treat infections of the genitourinary tract, including bladder, cervical, and vaginal infections.

Figure 8:
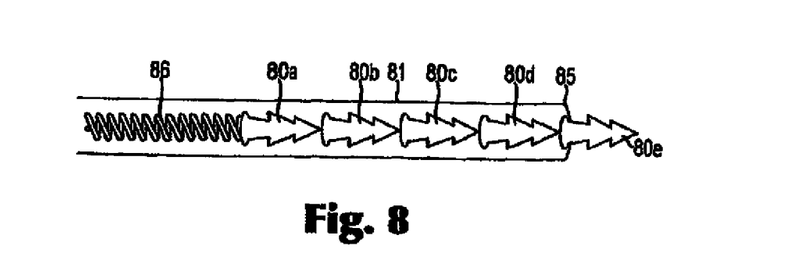
FIG. 8 is an illustration of a delivery device with drug-containing tissue penetrating members loaded in series in the device lumen.

In another embodiment of the invention the tissue penetrating members are delivered to a target pelvic tissue from the distal end of a hollow conduit, such as a catheter tube, rather than from the surface of a balloon. With reference to FIG. 8, the delivery device comprises a tube 81, a series of tissue penetrating members (80a-80d) loaded in the catheter tube 81, and an ejection member 86 for forcing the tissue penetrating members out of the distal end 85. FIG. 8 shows that ejection member 86 comprises a spring, but other mechanisms or features can be used to force the tissue penetrating members out of the distal end, such as a rod, a compressed air mechanism, or a pneumatic mechanism.

The tube 81 can also be made from a flexible material, sufficient to be manipulated and bent during insertion into a pelvic passageway, such as the urethra or vaginal tract. Exemplary flexible materials which can be made into catheter tubing include polyvinylchloride (PVC), polyurethane (PU), silicone, and polyester, which can provide adequate rigidity and flexibility for the insertion process. The surface of the catheter can also have a lubricant or a lubricious coating applied to the surface. The tube 81 can be configured for insertion into the urethra and can have a diameter in the range from 10 French to 28 French (F) (1 F-0.33 mm), with sizes in the range, of 12 F-16 F being common for use in adult humans, and having an inner diameter (lumen) in the range of about 1-3 mm. The tube can be larger for insertion into passageways such as the vagina, rectum, and uterus.

Figure 9:
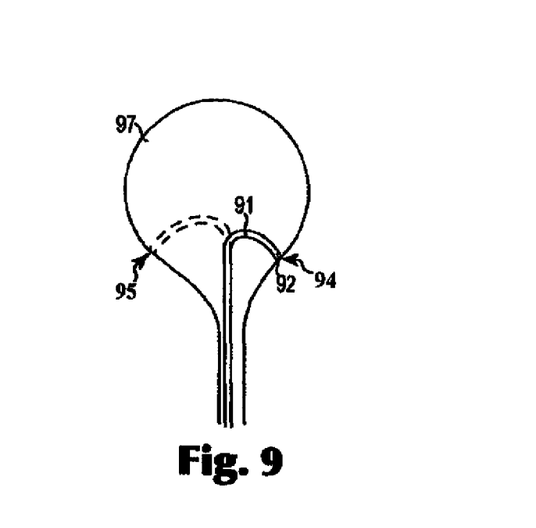
FIG. 9 is an illustration of a delivery device providing drug-containing tissue penetrating members to sites on the inner wall of a patient's bladder.

The embodiments as exemplified in FIGS. 8 and 9 can use tissue penetrating members having various configurations, including shapes that resemble a dart, a barb, a spear, a spike, a lance, or an arrow point. Any tissue penetrating members configuration as shown in FIGS. 2-7 can be used for the embodiments as exemplified in FIGS. 8 and 9.

Preferably, the tissue penetrating members used in the embodiments as exemplified in FIGS. 8 and 9 are larger than the tissue penetrating members used for the embodiments shown in FIGS. 2-7. For example, in some embodiments tissue penetrating members 80a-80e have a length in the range of about 500 μm to about 1 cm, about 1 mm to about 1 cm or about 2 mm to about 8 mm. In some embodiments tissue penetrating members 80a-80e have average diameter in the range of about 150 μm to about 5 mm, about 500 μm to about 5 mm, or about 750 to about 3 mm. Cross sectional areas and volumes of the tissue penetrating members can be determined accordingly.

Tissue penetrating members useful for the embodiments as exemplified in FIGS. 8 and 9 can be prepared from any absorbable polymer and therapeutic agent as described herein.

Referring to FIG. 8, to eject a tissue penetrating member from the distal end 85 of the device, the ejection member 86 is actuated. The ejection member 86 can be is actuated from an actuating member (not shown), such as a trigger, on the proximal end of the device. For example, a spring and flexible shaft combination can be used to eject a single tissue penetrating member from the distal end, and advance the series of tissue penetrating members in a distal direction following ejection. The actuating member can cause reloading of the spring for each ejection event, and the flexible shaft can progressively be advanced to cause movement of the tissue penetrating members. The distal end 85 can also include a flange or stopper to provide resistance to movement of the tissue penetrating members so they can be ejected with sufficient force and speed.

FIG. 9 illustrates delivery shows a delivery device that is inserted into the bladder and that uses a flexible tube 91 to eject tissue penetrating members into the bladder wall 97. In use, the distal end 92 of the flexible tube 91 is inserted into the bladder and placed at a first tissue location 94 on the bladder wall. The device is actuated to eject a tissue penetrating member from the distal end and into the bladder wall at a first tissue location 94. The distal end 92 of the flexible tube 91 is then moved to a second tissue location 95 on the bladder wall and the ejection step is repeated. The ejections can be performed a desired number of times at desired locations to provide a tailored tissue treatment. The tissue penetrating members release therapeutic agent in to the tissue over a desired time period.

What is claimed is:

1. A system for delivering a therapeutic agent to a pelvic tissue comprising:
    a delivery device configured to deliver tissue penetrating members to the pelvic tissue through a pelvic area passageway in a patient,
    the delivery device including a lumen, a proximal end, a distal end, and an ejection member including a spring configured to contact at least one of the tissue penetrating members to force the tissue penetrating members from the distal end,
    the tissue penetrating members being configured in a series that are disposed in the lumen in a proximal to distal arrangement, and configured to be deployed from the distal end of the delivery device and penetrate into the pelvic tissue, the tissue penetrating members including the therapeutic agent.

2. The system of claim 1, wherein the ejection member further includes at least one of a compressed air chamber, a hydraulic member, or a pneumatic pressure source.

3. The system of claim 1, wherein at least one of the tissue penetrating members has a length from a proximal end to a distal end in a range of about 500 µm to about 1 cm, about 1 mm to about 1 cm or about 2 mm to about 8 mm.

4. The system of claim 1, wherein at least one of the tissue penetrating members has an average diameter in a range of about 150 µm to about 5 mm, about 500 µm to about 5 mm, or about 750 µm to about 3 mm.

5. The system of claim 1, wherein the delivery device is configured for insertion through at least one of a urethra, a vagina, an anus, or a uterus.

6. The system of claim 1, wherein at least one of the tissue penetrating members includes an absorbable polymeric material and a therapeutic agent mixed with or surrounded by the polymeric material, the therapeutic agent releasable from the tissue penetrating member following implantation in tissue.

7. The system of claim 1, wherein at least one of the tissue penetrating members includes an elongated member, the elongated member includes a proximal end, a distal end, and a length between the proximal end and the distal end, the length being in a range of about 50 µm to about 2000 µm or about 100 µm to about 1500 µm, or about 200 µm to about 1000 µm, or about 250 µm to about 750 µm.

8. The system of claim 1, wherein at least one of the tissue penetrating members has an average diameter in a range of about 15 µm to about 1000 µm, or about 25 µm to about 750 µm, or about 50 µm to about 500 µm, or about 100 µm to about 250 µm.

9. The system of claim 1, wherein at least one of the tissue penetrating members includes an elongated member, the elongated member includes a proximal end, a distal end, and a length between the proximal end and the distal end, the length being in a range of about 500 µm to about 1 centimeter.

10. The system of claim 1, wherein at least one of the tissue penetrating members has an average diameter in a range of about 150 µm to about 5 mm.

11. The system of claim 1, wherein at least one of the tissue penetrating members has a volume in a range of about 3000 µm$^3$ to about 0.55 µm$^3$, or about 0.01 µm$^3$ to about 0.45 µm$^3$, or about 0.05 µm$^3$ to about 0.45 µm$^3$.

12. The system of claim 1, wherein at least one of the tissue penetrating members has at least one of a dart, a barb, a spear, a spike, a lance, or an arrow point shape.

13. The system of claim 1, wherein at least one of the tissue penetrating members includes one or more projections on an elongate surface of the tissue penetrating members.

14. The system of claim 13, wherein the one or more projections are in a form of at least one of tines, barbs, or ridges.

15. The system of claim 1, wherein the tissue penetrating members include an absorbable polymeric material selected from at least one of polyhydroxyalkanoates, poly-4-hydroxybutyrate (P4HB), poly(3-hydroxyvalerate, and poly (hydroxybutyrate-co-hydroxyvalerate), polyesters, polylactic acid, poly(lactide-co-glycolide), polycaprolactone, poly (valerolactone), poly(glycolic acid), poly(glycolide), and poly(dioxanone); polyorthoesters, polyalkeneanhydrides, poly(sebacic acid), polyanhydrides, polyphosphazines, polysaccharides, hyaluronic acid, alginate, dextran, starch, amylopectin, cellulose, xanthan, pullulan, chitosan, pectin, inulin, or heparin.

16. The system of claim 1, wherein the therapeutic agent comprises at least one of an antimuscarinic agent, oxybutynin, tolterodine, solifenacin, hyoscyamine, a nerve toxin, Botulinum toxin, chemotherapeutic agents, N,N',N'-triethylenethiophosphoramide (ThioTEPA), adriamycin (doxorubicin, ADM), epirubicin (EPI), mitomycin C (MMC), valrubicin (AD32), pirarubicin (THP), gemcitabine, apaziquone (EOQUIN), and VICINIUM (anti-Ep-CAM humanized scFv-exotoxin A fusion protein), antiproliferative agents or angiogenesis inhibitors, taxol, rapamycin, tacrolimus, ABT-578, everolimus, paclitaxel, taxane, 13-cis retinoic acid, and 5-fluorouracil, a steroid, dexamethasone, cortisone, hydrocortisone, prednisone, prednisolone, triamcinolone methylprednisolone, beclomethasone, betamethasone, chloroprednisone, corticosterone, desoxycorticosterone, estradiol, fluorocortisone, androsterone, aldosterone, methyl testosterone, norethandrolone, estriol, estrone, hydroxyprogesterone, an antibiotic, amoxicillin, ephalexin, cefadroxil, cefuroxime, loracarbef, cefixime, pivmecillinam, trimethoprim-sulfamethoxazole, trimethoprim, ofloxacin, ciprofloxacin, norfloxacin, levofloxacin, doxycycline, tetracycline, minocycline, gentamicin, tobramycin, amikacin, nitrofurantoin, or azithromycin.

17. The system of claim 1, wherein the delivery device including a flexible catheter tube.

18. A method for delivering a therapeutic agent to a pelvic tissue comprising:
    inserting a delivery device through a pelvic area passageway in a patient to deliver tissue penetrating members, the delivery device including a lumen, a proximal end, a distal end, and an ejection member including a spring configured to contact at least one of the tissue penetrating members to force the tissue penetrating members from the distal end, a series of tissue penetrating members disposed in the lumen in a proximal to distal arrangement, the tissue penetrating members configured to be deployed from the distal end of the deliver device and penetrate into the pelvic tissue, the tissue penetrating members including the therapeutic agent;
    ejecting the tissue penetrating members from the distal end and into the pelvic tissue;
    moving the distal end of the delivery device to a different tissue location;
    repeating the step of ejecting; and releasing the therapeutic agent to the tissue from the tissue penetrating members.

* * * * *